(12) United States Patent
Nervino et al.

(10) Patent No.: US 10,945,388 B1
(45) Date of Patent: Mar. 16, 2021

(54) IRRIGATION MANAGEMENT SYSTEM

(71) Applicant: Blake Nervino, Turlock, CA (US)

(72) Inventors: Blake Nervino, Turlock, CA (US);
William Espinoza, Turlock, CA (US)

( * ) Notice: Subject to any disclaimer, the term of this patent is extended or adjusted under 35 U.S.C. 154(b) by 0 days.

(21) Appl. No.: 16/711,136

(22) Filed: Dec. 11, 2019

Related U.S. Application Data

(63) Continuation-in-part of application No. 16/043,891, filed on Jul. 24, 2018, now Pat. No. 10,524,430.

(60) Provisional application No. 62/650,166, filed on Mar. 29, 2018.

(51) Int. Cl.
  *A01G 25/16* (2006.01)
  *A01G 27/00* (2006.01)
  *G01N 33/24* (2006.01)

(52) U.S. Cl.
  CPC ......... *A01G 25/167* (2013.01); *A01G 27/003* (2013.01); *A01G 27/008* (2013.01); *G01N 33/246* (2013.01); *G05B 2219/2625* (2013.01)

(58) Field of Classification Search
  CPC ..... A01G 25/167; A01G 27/003; A01G 27/02
  See application file for complete search history.

(56) References Cited

U.S. PATENT DOCUMENTS

| | | | |
|---|---|---|---|
| 6,401,742 B1* | 6/2002 | Cramer | A01G 25/167 137/78.3 |
| 7,997,294 B2* | 8/2011 | Murray | A01G 27/003 137/78.3 |
| 2005/0194461 A1* | 9/2005 | Goldberg | A01G 25/167 239/63 |
| 2012/0239211 A1* | 9/2012 | Walker | A01G 25/16 700/284 |
| 2013/0319089 A1* | 12/2013 | le Roux | A01G 25/167 73/73 |
| 2015/0361630 A1* | 12/2015 | Appelboom | E02B 11/00 405/104 |
| 2017/0061052 A1* | 3/2017 | Gates | A01G 25/167 |
| 2017/0270624 A1* | 9/2017 | Rooney | G06Q 30/018 |

* cited by examiner

*Primary Examiner* — Hongmin Fan
(74) *Attorney, Agent, or Firm* — Thomas M. Freiburger

(57) ABSTRACT

An irrigation management system monitors irrigation parameters, including progress of flood irrigation water admitted onto a farm field, water levels in ditches, basins or boxes, soil moisture, water usage and other important factors. In flood irrigation a series of small, inexpensive sensors detect the presence in each of the sensor locations in a field, and each sends a signal when water first reaches the sensor. In a preferred form the sensor communicates by long-range radio communication either directly with a hub or gateway, or by sending a transmission that is relayed from location to location and ultimately to the hub or gateway. All aspects of irrigation water need, availability, task completion, pipe and equipment status, and water usage are monitored and communicated to the farmer. The system allows efficient water management and reliable and responsible irrigation at all irrigated fields.

7 Claims, 15 Drawing Sheets

IRRIGATION MANAGEMENT SYSTEM

This application is a continuation-in-part of application Ser. No. 16/043,891, filed Jul. 24, 2018, now U.S. Pat. No. 10,524,430, issued Jan. 7, 2020, which claimed benefit of provisional application No. 62/650,166, filed Mar. 29, 2018.

BACKGROUND OF THE INVENTION

This invention concerns irrigation water management, on farms and in irrigation districts, especially including flood irrigation, and also concerns groundwater replenishment.

Irrigation of a farm field by flood irrigation, typically on a relatively flat field with a slight downward grade, is common in some geographical areas. For example, many crops are irrigated by flood irrigation in the Central Valley of California. In most recent years, water has been in short supply.

For such irrigation, water stored behind dams and directed through irrigation channels or pipes is applied by releasing the water at the higher end of a field and allowing that water to flow by gravity over all areas of the field. The field may be as small as about one-half acre or it could be many acres. Typically the field will have one crop, the water needs of which should be consistent in all areas. However, variations occur in surface contour, soil type and subsurface geology and, for example, some areas will drain water more quickly, with others holding water longer on the surface.

An objective of the invention is to maximize efficiency of water use in management of flood irrigation and other forms of irrigation on farms. In flood irrigation this involves sensing the presence of surface water at a series of different positions in a field, letting the farmer know when water reaches a particular area of the field and, optionally, how long the water remains. Also, related objectives are to measure soil moisture at various points and to determine water surface levels, including upstream and downstream of a gate, all to provide the farmer with complete and thorough information regarding an irrigation system to enable the farmer to manage irrigation more precisely and efficiently, saving water and time.

A further objective of the invention is irrigation water management and monitoring in irrigation districts, including use of surface water and groundwater, and the replenishment of groundwater.

The following patents and applications may have some relevance to the invention: U.S. Pub. Nos. 2017/0127622, 2016/0219805, 2016/0183484, 2014/0361887, 2014/0225747; U.S. Pat. Nos. 8,739,830, 8,643,495, 8,326,440; China Pub. Nos. CN 105123446, CN 104542197 and CN 103210819.

SUMMARY OF THE INVENTION

Pursuant to one aspect of the invention an irrigation management system monitors progress of flood irrigation water admitted onto a farm field. A series of small, inexpensive sensors detect the presence in each of the sensor locations in the field, and each sends a signal when water first reaches the sensor. In a preferred form the sensor communicates by long-range WiFi (LORA) or similar long-range wireless communication, either directly with a hub or gateway, or by sending a transmission to be relayed from sensor location to sensor location and ultimately to the hub or gateway. In that form each sensor can receive signals as well as send signals. The system allows efficient water management and reliable irrigation at all areas of an irrigated field. An important feature of the invention is construction of the sensor device. The sensor in one implementation is formed of inexpensive plastic plumbing pipe, such as PVC pipe, with an internal diameter of at least two inches, or a range of about two to four inches. The bottom end of the pipe section is fully closed, either with an integral closure or a cap, and the housing has a top cap which is removable. When the top cap is installed the sensor unit is fully sealed against intrusion of moisture. The top cap may be threaded, or simply fitted closely onto the top end of the section of plumbing pipe. The housing could be formed of other materials, such as custom injection-molded components if desired.

Near the bottom of the sensor device, approximately one-half inch to one inch above the bottom end, are a pair of conductor probes isolated from each other and extending from the interior to the exterior of the housing, positioned to sense surrounding water that reaches a preselected depth threshold (such as one-half inch to one inch). Note that only one sensor need be at the desired sensing level, the other being lower and optionally integral with a spike extending downward from the housing to hold the unit at the selected location on the ground.

Within the interior of the housing is a battery, an antenna, a microprocessor and a radio transmitter (LORA or other long-distance wireless), as well as a circuit connected to the two external conductor probes for detecting the presence of surrounding water. The sensor circuit includes the battery and an activator (which may be the microprocessor) such that in absence of surrounding water an electrical potential exists between the external conductor probes, without current flow, but in the presence of surrounding water the circuit is closed, causing the processor to fully awaken and to send a wireless signal indicating the presence of water.

These small, compact sensors are placed at a series of locations on a field to be subjected to flood irrigation. They enable the farmer to monitor, with resolution as desired, effected by the number and density of sensors in the field, the irrigation water reaching each of many different areas of the field. When irrigation water is admitted from the high end of the field to flood the field, the water sensors at respective positions in the field will send a signal upon water reaching the preselected depth surrounding the respective water sensor, thereby providing information as to progress of irrigation water in reaching different areas of the field.

In one implementation of the invention, the sensors, or at least some of them, can receive and transmit, and a signal from one sensor can be passed on in chain-like fashion successively to and from further sensors until the signal reaches the hub or gateway. This enables the signal to travel as far as desired, as long as the chain segments are functional, which will require each of the sensors in a communication path be "awake" to the extent of receiving a signal. This could be only selected ones of the sensors sufficient to establish a live path.

Alternatively, all sensors could remain quiescent until water awakens them, and hubs could be placed as needed to enable the communication path. In an alternative implementation each sensor is capable of sending a signal that will reach the hub or gateway directly, not involving intermediary sensors.

Each sensor can include a GPS transmitter if desired, for reporting its position with a transmitted signal. This will increase a sensor's awake time slightly, as the sensor acquires its GPS position, then the sensor will go back to sleep. The use of GPS enables a map to be presented on the farmer's screen (whether a PC or a mobile device), showing an accurate location of each sensor on the field. With the sensors being small, the GPS locator feature can be important in finding a sensor. As an alternative, however, the sensors can be noted as to position when placed (such as using a separate hand-held GPS device, such as on a smartphone), which will also enable a map to be created. Each signal from a sensor is unique and identifies the particular sensor.

Further, a solar cell can be provided on or near each sensor, to charge a rechargeable battery in the unit.

In one embodiment the gateway can send a confirming signal back to a sensor, indicating the sensor's transmission has been received. In this case all sensors are receivers as well as transmitters.

The microprocessor used in the unit can be a Particle Photon Wi-Fi connected microcontroller, although other processors can be used.

The invention further encompasses aspects of irrigation water monitoring and management for a farm or group of farms or other irrigated land area such as in an irrigation water district. Where groundwater is used as a primary or secondary source of irrigation, groundwater depletion is a concern, and the invention encompasses a system for monitoring approximately an amount of groundwater replenishment occurring on farm fields due to irrigation, and also replenishment of groundwater via groundwater replenishment basins. Further, the invention encompasses monitoring, from a central location, level of water in a series of irrigation water delivery pipes, canals or ditches that convey irrigation water to a series of farms in irrigation districts or other irrigation water distributing organization. Monitoring can be via wireless data transmission from depth sensors and flow meters. Where groundwater is used, the invention provides an approximation of replenished groundwater from irrigation, especially flood irrigation, which can be balanced against water usage on a farm or group of farms.

It is accordingly among the objects of the invention to provide a simple and conveniently used farm management system, particularly to monitor many different points in fields with regard to flood irrigation and water status, for providing comprehensive data to the farmer, increasing the farmer's efficiency and precision in managing irrigation and resulting in much more efficient use of time and of water and assurance that crops are receiving the correct amount of water. Another object is monitoring irrigation water status, levels and use from a central location, such as in an irrigation district, which can be along with electronic monitoring of groundwater replenishment via irrigated fields or groundwater replenishment basins. These and other objects, advantages and features of the invention will be apparent from the following description of a preferred embodiment, considered along with the accompanying drawings.

DESCRIPTION OF PREFERRED EMBODIMENTS

The system of the invention in one aspect is an open platform hub and spoke, or combination mesh and hub/spoke, connected farm utilizing long range Wi-Fi radio technology. As explained above, the system includes special sensors and transmits information to a central hub, or gateway, the farm having many of these sensors in different fields. The system provides comprehensive irrigation water status information, including real-time data, enabling the farmer efficiently to manage the use of flood irrigation water and to detect problems involving broken pipelines, overflows or accidently flooded areas. The presence of water at any of the many sensors can be sent to the farmer or manager via text message or other forms of communication in a portable smartphone or other device, including urgent alerts in the event water is detected where it should not be present. The system allows the farmer to prevent over watering, as well. Water costs can be greatly reduced, as well as labor costs.

In an embodiment of the system level sensors are also employed, providing the farmer data on levels at strategic locations such as at basins or channels upstream and downstream of valves, for water flow and availability status. Further, soil moisture sensors can be included in some fields.

The system of the invention can monitor other aspects of the farm, such as the use of equipment, and the location and movement of equipment.

Figure 1:
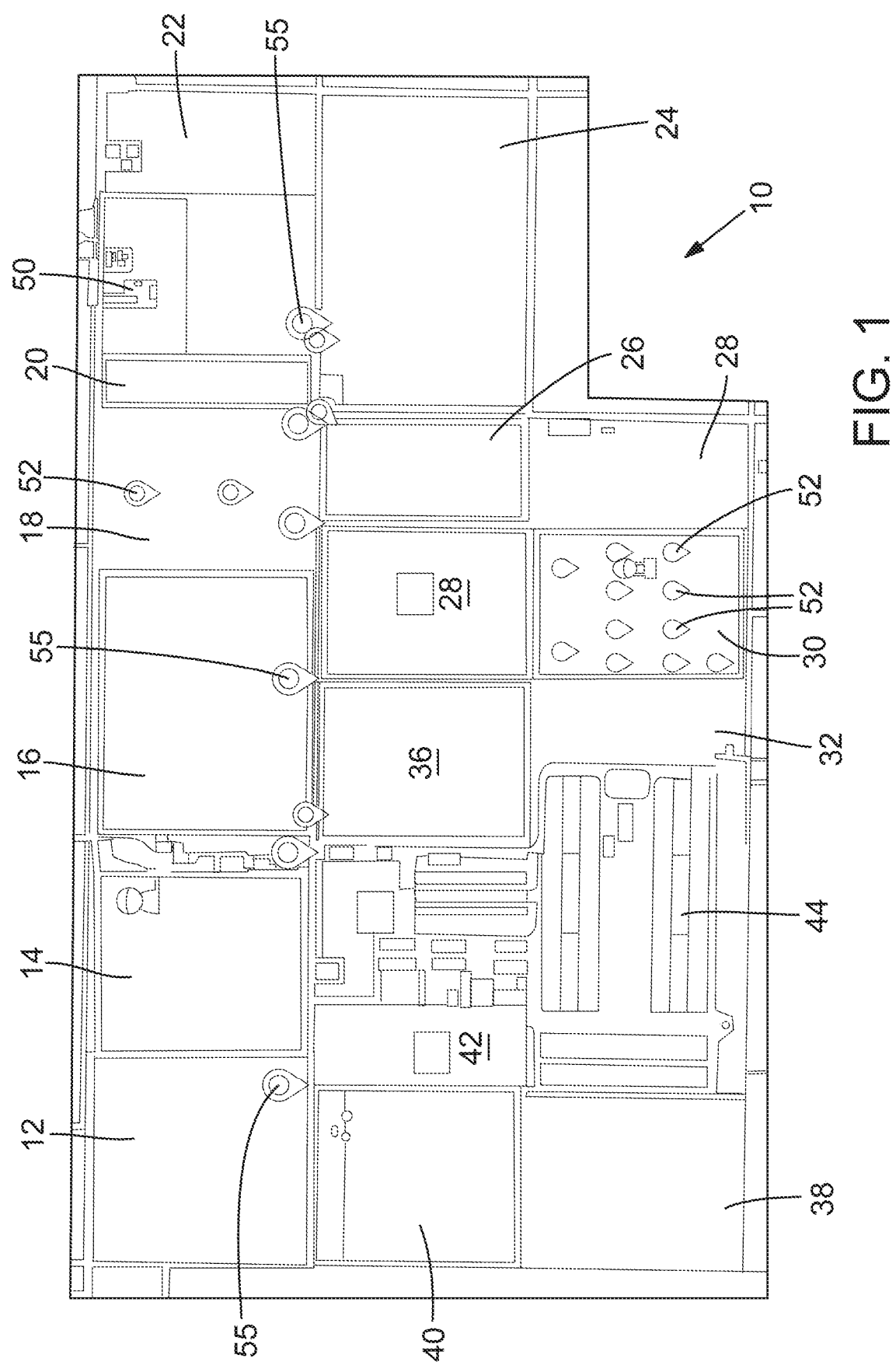
FIG. 1 is an aerial plan view of a farm exemplifying the system of the invention.

FIG. 1 shows an example of a farm 10, in aerial view, using the system of the invention. The farm has various fields typically with different crops, the fields indicated as 12, 14, 16, 18, etc. Barns, sheds and storage for equipment, grain, etc. are indicated within rectangular areas at 44 and 46. A farmhouse and associated buildings are shown at 50. A gateway for the system can be located in the farmhouse, in other buildings that might be located in the areas 44 or 46, or in any sheltered housing at a convenient, accessible location.

FIG. 1 also shows, as an example, locations of various sensors on the farm, sensors that can transmit data signals to the hub or gateway of the system. A series of eleven sensors 52 are shown in the field 30, at positions determined to be critical indicators of the progression and distribution of flood irrigation across the field, the field typically having a slight downward grade from the flooded end to the lower end. The field 18 is shown with a series of sensors 52 at selected locations in the field, and similar sensors 52 are shown in several other fields. These are water presence sensors, although they could have other features as well, as discussed below. In the field 30 the sensors are shown in a view that might be presented on a screen of a computer or portable device. Five of the sensors 52 near the higher end of the field have blue indicators, to show water sensed at those locations. The other sensors in the field are shown dry.

Other sensors are shown at 55, arranged along an irrigation ditch or pipeline. These sensors will report water level, which also provides an inference of the level of pressure being exerted on a pipeline. In some cases a pipeline can only withstand a predetermined pressure, and the system can provide alarms if that pressure is being approached, or exceeded. This can be an urgent situation and can be addressed by the farmer to avoid a pipe or ditch failure.

In FIG. 1 a field 24, typically an orchard, has been sprayed, so that entry by farm personnel should be prohibited for a prescribed period, as indicated in the drawing. This can be initiated using a sensor on the tractor used in the spraying, including an input of the duration of time for the prescribed period.

Figure 2:
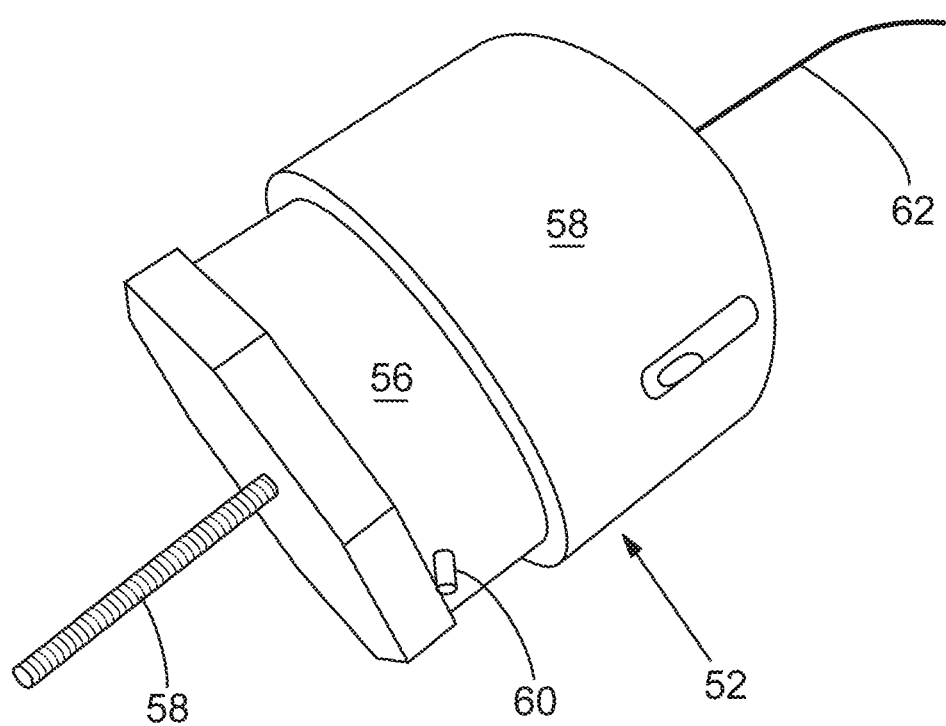
FIG. 2 is a perspective view of a water presence sensor as a key component of the system of the invention.
Figure 3:
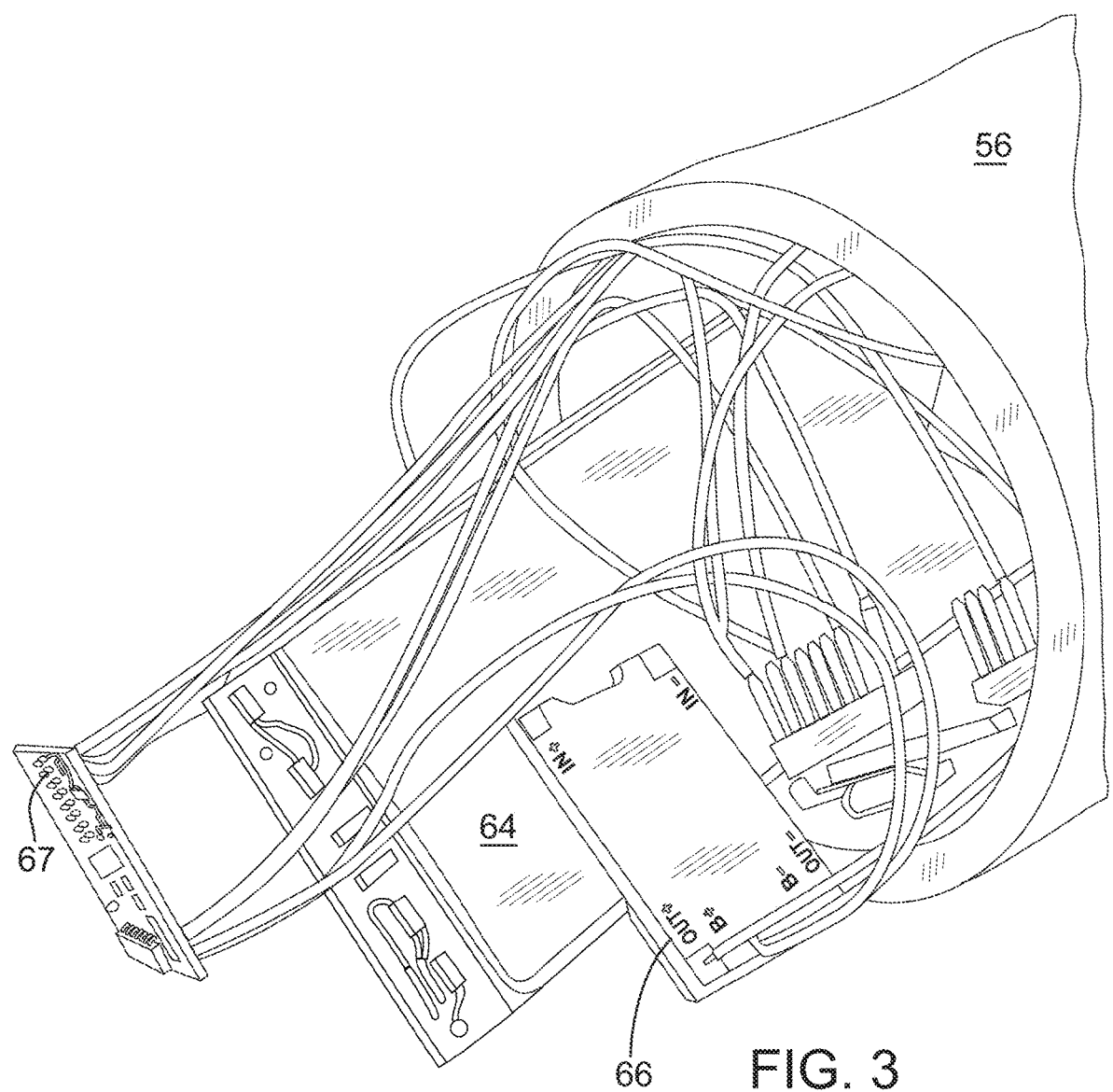
FIG. 3 is a perspective view of the sensor with cap removed, showing components contained inside the waterproof capsule.
Figure 7:
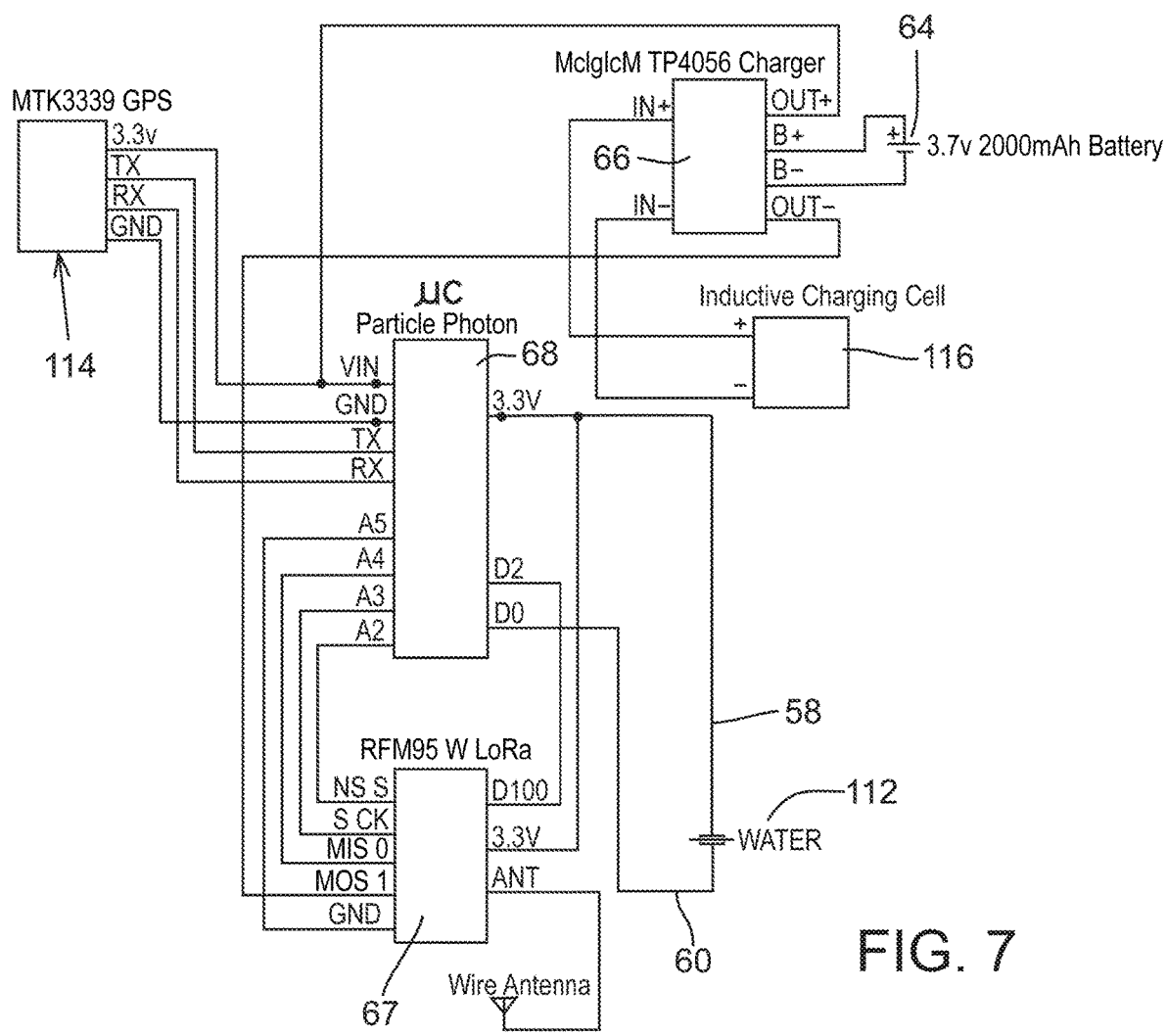
FIG. 7 is a schematic circuit diagram for the sensor.

An embodiment of the water presence sensor 52 is shown in FIGS. 2 and 3, with an example of one form of preferred circuitry shown in FIG. 7. FIG. 2 shows the sensor device 52, as one example, formed in a simple and relatively low cost construction using PVC pipe components 56 and 58. The cap 58 can be connected to the base 56 by screw threads, or simply by a close fit, with the two components tightly held together in waterproof relationship. The sensor device has a pair of contacts for sensing the presence of water, and these can be a bottom prong 58 that anchors the device in the ground, as one contact, and a second contact 60 at a selected height for activating the electronics of the device when water reaches the level of that contact 60. An antenna 62 can extend out the top of the cap, or an internal antenna can be used. The contacts and antenna are sealed to the housing so as not to allow intrusion of water. Instead of the PVC components, the sensor casing can be an off-the-shelf plastic electronics box with openable, sealed cover. Many such boxes are available.

Figure 8:
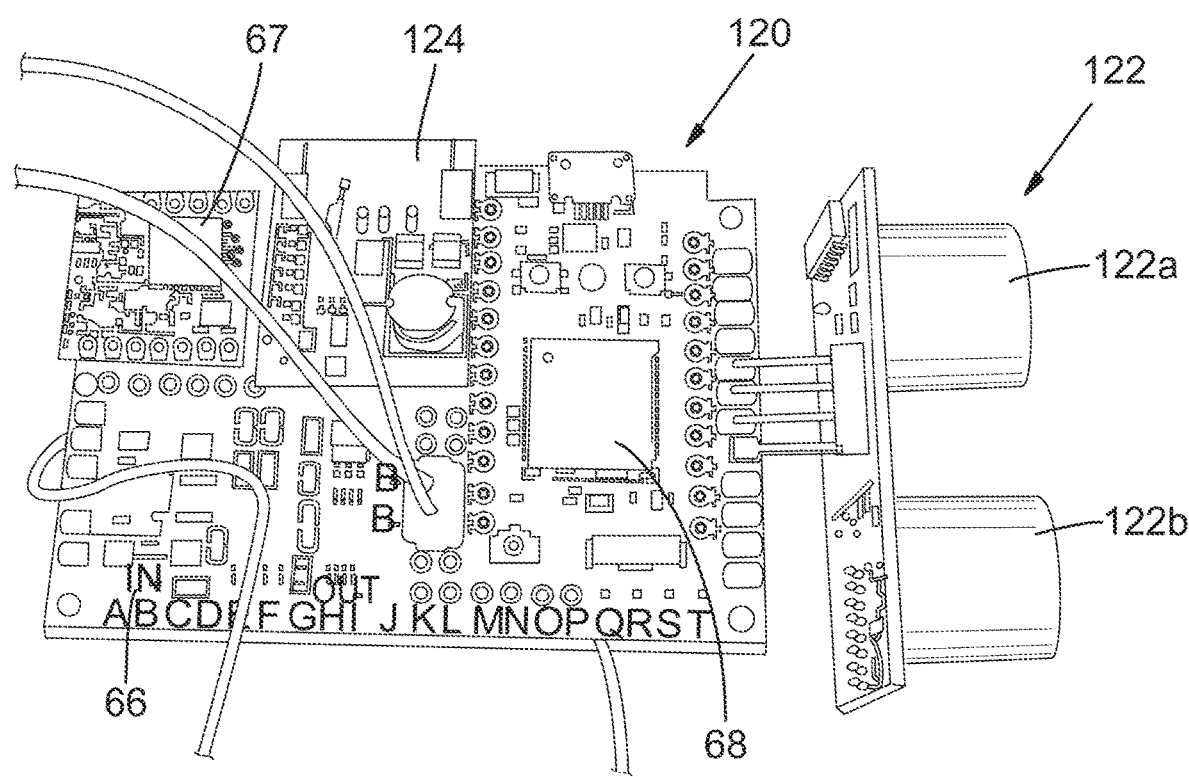
FIG. 8 is a plan view showing a printed circuit board according to one implementation of the invention.

In FIG. 3 the cap 58 has been removed, revealing electronic components in this preferred embodiment, contained within the sealed interior. These include a battery 64, which can use lithium and be rechargeable (or other types of battery, such as four AA cells, non-rechargeable). A charge controller PCB is shown at 66 in this embodiment (TP4056-Protect shown here), and at 67 is the LORA radio PCB. FIG. 8, discussed below, shows a main PC board for one implementation of the invention. One example of a processor for the system is a Particle Photon Wi-Fi connected microcontroller, capable of LORA transmission.

Figure 4:
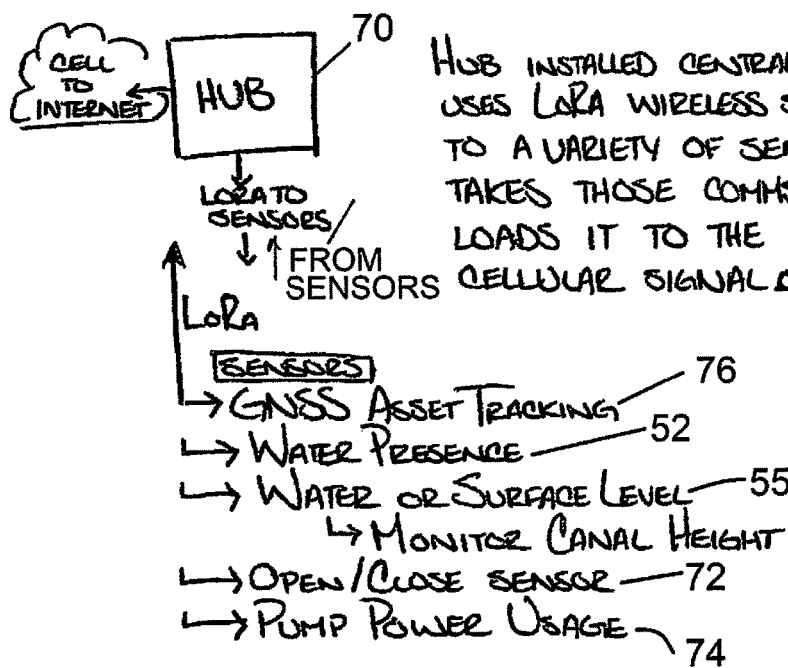
FIG. 4 is a schematic drawing indicating concepts of the invention.

The diagram of FIG. 4 indicates general layout of the system and various functions. The hub or gateway of the system is indicated at 70, preferably located centrally on the farm to receive wireless signals from a variety of sensors on the farm. As indicated, the hub receives data and loads the data to a cloud based server via cellular signal or via an available local Wi-Fi system to the Internet. The data can then be retrieved by the farmer or farm manager from any location, and alerts or alarms can be delivered to the farmer if something urgently needs attention.

FIG. 4 also indicates signals going to and from the hub 70, the hub communicating with various sensors. Water presence sensors are noted at 52, but also indicated are water surface level sensors 55, discussed above in connection with FIG. 1, for monitoring water in a pipeline or in a canal or basin or irrigation ditch delivering water. Further, the hub 70 can be connected, preferably with two way communication, to valve sensors 72 to report the status of valves, and pump power usage indicators 74. Further, GNSS (global navigation satellite system) devices can be installed on farm equipment and various other assets of the farm where tracking would be useful, as indicated at 76. For example, tractors can each be equipped with GNSS, as can implements towed by tractors, and various other mobile assets of the farm.

Figure 5:
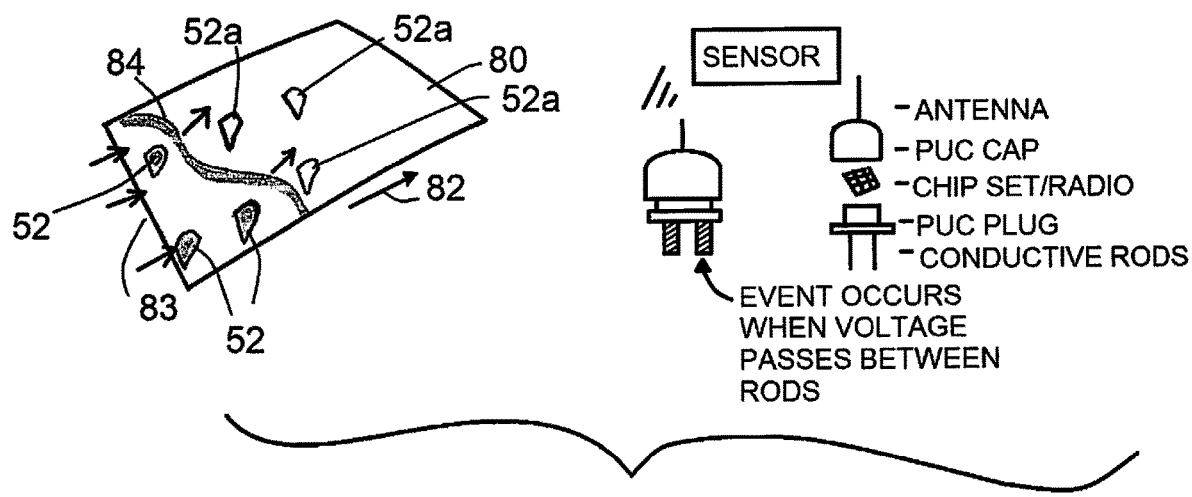
FIG. 5 is a drawing indicating schematically a farm field and progression of flood irrigation across the field.

FIG. 5 schematically illustrates a farm field 80, which trends downhill in the direction of the arrow 82. Irrigation water is released at the top end 83 of the field, as indicated. The water progresses along an advancing front indicated at 84. Water presence sensors 52 to which the water has advanced are shown shaded in the drawing, and these have sent a signal to the hub of the system, since the two exterior contacts on each of these sensors have closed the circuit and activated the electronics. Additional sensors 52a in FIG. 5 have not yet been activated. This will show any irregularities or anomalies in the pattern of water advancement, i.e. in watering the crops in the field. The data can be presented pictorially on a computer screen or the screen of a smartphone or other portable device for observation by the farmer. There may be sensors that have not been activated, thus areas not reached by water, or there may be some that require longer than expected to be activated. This can indicate the need for some adjustments to the surface grade.

Figure 6:
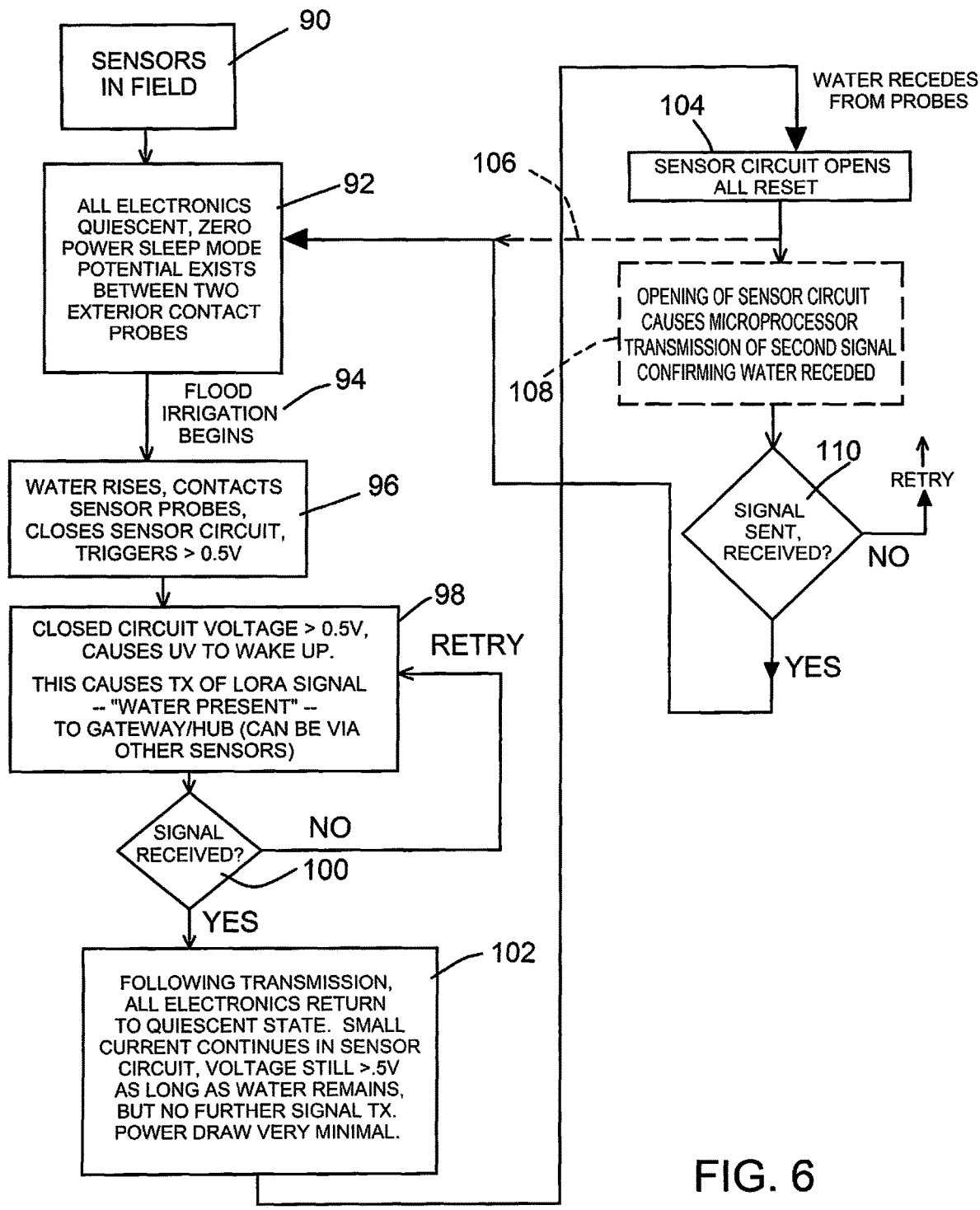
FIG. 6 is a flow chart indicating functions of the system.

FIG. 6 is a simplified flow chart illustrating operation of the system of the invention in the block 90. The more densely the sensors are placed, the higher the resolution provided to the farmer as to wetting data as the flood irrigation is advanced on the field. After initial testing and calibration, the block 92 shows that all electronics of the sensors are quiescent, drawing almost no power at this point (preferably less than 20 milli Amps). An electrical potential exists between the two exterior contact probes, but without current flow. Flood irrigation begins as indicated at 94. The irrigation water advances down the field, such that water rises and contacts the sensor probes of the sensors, one by one. This is effective to close the sensor circuit of each sensor which has been reached by the water, as indicated in the block 96. This triggers flow of current, at a voltage of greater than a threshold of 0.5V.

As in the block 98, with the circuit closed and voltage exceeding 0.5V, this wakes up the microprocessor. The microprocessor causes a signal to be transmitted (e.g. a LORA signal), indicating "water present". This signal goes to the gateway or hub 70. It may not be sent directly to the hub; in an embodiment of the invention it can be sent successively from sensor to sensor to reach the gateway 70, provided the sensors are both receivers and transmitters.

In a preferred implementation of the system, receipt of the signal at the hub 70 must be confirmed or the signal will be retransmitted by the microprocessor in the sensor. See the decision block 100.

As in the block 102, after the signal has been transmitted and received, all electronics return to the quiescent state, except that a small current continues in the sensor circuit.

The voltage over the threshold of 0.5V will exist, but with a very small flow of current and low power draw, as long as water remains. No further signal will be transmitted.

After the water recedes below the point at which the sensor's contacts are wetted, the sensor's circuit opens, as in the block 104. In one form of the system the electronics of the sensor are all reset at this point, returning status of the sensor to the block 92 as indicated the dashed line 106. However, in another implementation indicated in the optional block 108, the opening of the sensor circuit will be an event that causes the microprocessor to transmit a second signal, different from the first signal, and confirming that the water has receded. This will give the farmer additional data indicating the length of time during which the water was present. Again, as noted in the decision block 110, the system can require confirmation that the signal was received. Once that has occurred, the status of the sensor returns to block 92.

FIG. 7 shows a preferred embodiment of the electronics contained in a sensor 52. The sensor's probes are indicated by lines 58 and 60 in the diagram, which can be connected by water as noted at 112. The microprocessor, which can be a Particle Photon Wi-Fi connected microcontroller, is denoted at 68. A LORA transmitter of the sensor is shown at 67. A GPS can be included in the sensor, as discussed above, and this is indicated in the diagram at 114. The battery 64 is also shown, indicated as a rechargeable battery which in a preferred embodiment is charged inductively; FIG. 7 indicates an inductive charging coil 116 in the sensor in a position to be charged from outside the housing, this coil 116 being connected to a battery charge controller 66. Other batteries can be used, such as AA non-rechargeable cells. Any source of approximately 5V is adequate.

As indicated in the schematic, the closing of the circuit via the conductor probes 58 and 60 causes a flow of current at 3.3 volts in the microprocessor 68, and the microprocessor activates the LORA transmitter 67, again with current flowing at a voltage of 3.3 volts the transmitter. Further, the microprocessor controls the GPS 114, activating the GPS to send a signal only when controlled by the microprocessor to do so. Again, current is shown flowing at 3.3V. The GPS receives satellite position data and transmits that data to the microprocessor, as indicated in the drawing.

The components of the sensor for one embodiment of the invention are also shown in FIG. 8, in this case a water depth sensor. FIG. 8 shows a printed circuit board 120, in this case connected to an ultrasound surface distance sensing unit 122. This includes an ultrasound transmitter 122a and receiver 122b, for determination of distance from the sensor to a surface, e.g. a water surface. Otherwise, the PC board 120 has most of the components shown in FIG. 7 (without GPS). The LORA radio transmitter is shown at 67, the microprocessor is at 68 and the charge controller is shown at 66. The device shown at 124 in FIG. 8 is a 3.5V to 5V converter, which is needed for the ultrasound surface distance measuring device 122. These electronics can be the internal components of the depth sensors 55 discussed above.

Figure 8A:
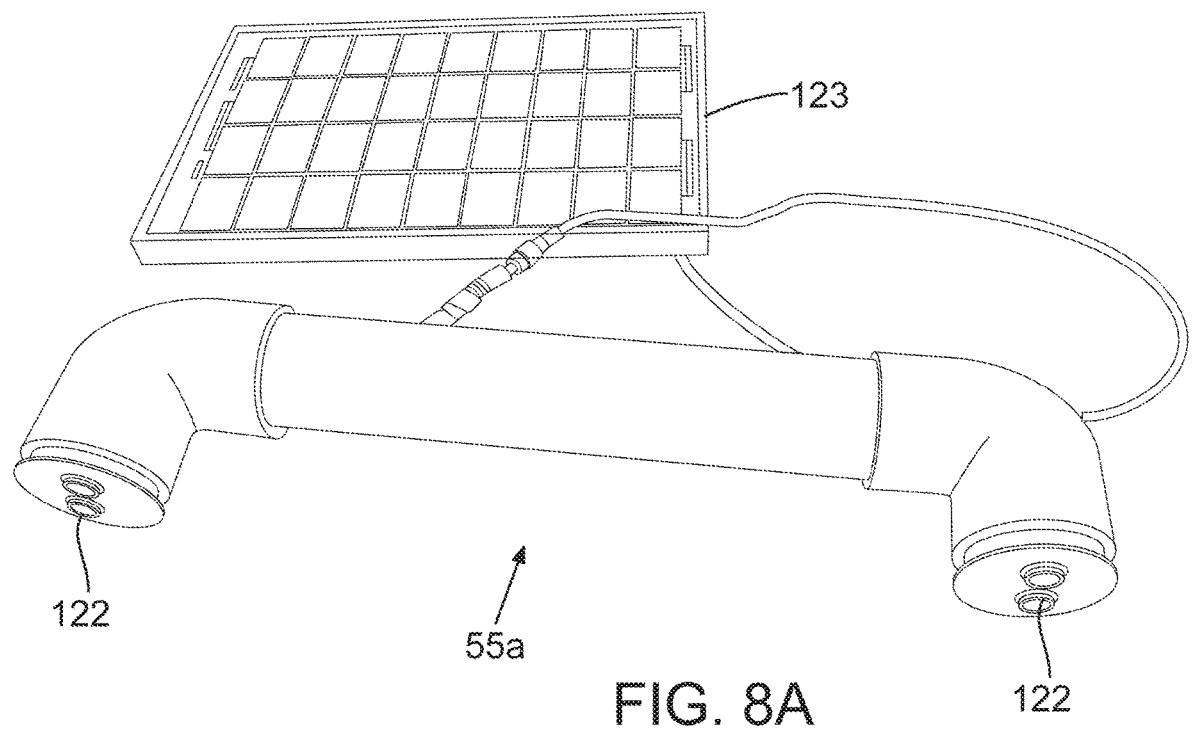
FIG. 8A is a perspective view of a differential water level sensor in one embodiment of the invention.

FIG. 8A shows an implementation of a dual depth sensor 55a with the electronics described above for sensing depth by distance to the water surface. The two-sensor device is used for differential depths, such as in a box, at upstream and downstream sides of a gate valve, to provide important information to the farmer. One main PC board (120, above) can serve both ultrasound units, with only the specific ultrasound electronics duplicated. The embodiment shown has a housing of PVC components, and is connected to a solar array 123 for recharging the battery of the device during the day.

Figure 9:
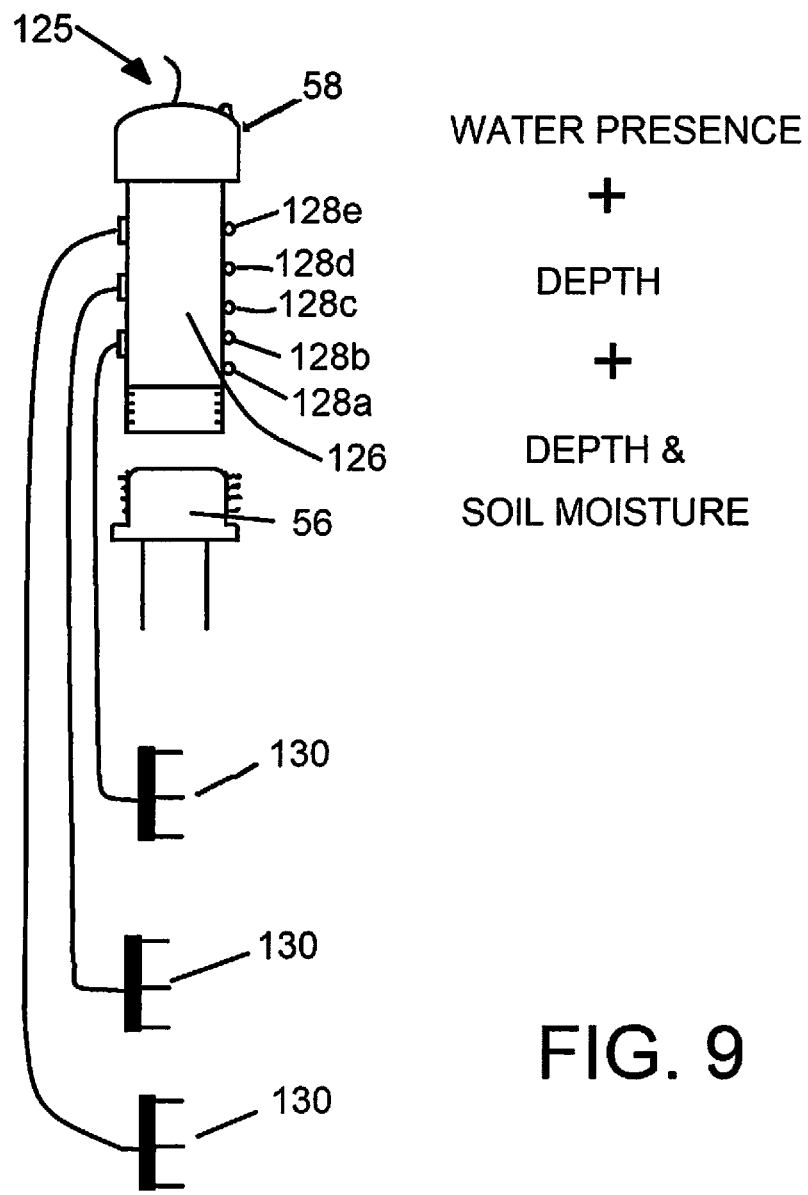
FIG. 9 is a schematic elevation view indicating another embodiment of a sensor of the invention.

FIG. 9 shows schematically another form of sensor 125 that can be included with the system of the invention. The sensor can have a base and cap 56 and 58 similar to the sensor 52 described above, but with a taller profile, an additional section of the sensor being shown at 126. Here, the sensor 125 can sense a successive series of water levels, to indicate depth or pressure. Thus, contacts are shown at 128a, 128b, 128c, 128d and 128e. The signal sent by the microprocessor in this case will indicate the level reached by the water. Further, the sensor 125 can include sensing of soil moisture capacity. Three fork-shaped probes 130 are indicated as connected to the device 125, each to indicate the capacity of the soil-held moisture at a different level. A potentiometer signal is received and fed to the microprocessor to provide moisture at each depth, with this data then sent to the hub or gateway.

An important aspect of the invention is that the water presence sensor as described above constitute the basic sensor architecture for all sensor devices in the system. All the basic components are the same for water presence sensors, water level sensors, soil moisture sensors and intermediate hubs. These basic components are the microprocessor, the LORA communication device, PC board, antenna and battery (which may be rechargeable, with charging circuitry, or can be recharged with a solar PV array nearby). GPS may be included in all. Each type of specific purpose sensor has its own additional component(s), as for moisture sensing, level sensing, etc. Some of the devices, as noted above, can have off-the-shelf electronics boxes as housings. In particular the gateway or hub 70, moisture sensors and water level sensors can be in such housings, as can be the water presence sensors.

One embodiment of a preferred farm system of the invention includes the water presence sensors 52, water level sensors 55 (using the ultrasound distance measurement device 122), soil moisture measurement devices, a gateway to receive transmissions from the various sensors, and, optionally, intermediary hubs as needed to relay signals from the sensors to reach the gateway, in the event sensor to sensor relayed "mesh" communication is not used. The farmer is thus provided with comprehensive data concerning irrigation conditions on the farm, as well as water available at any given time, and rate of water use. This information is available in real time, with alerts to the farmer in the event of urgent situations. Alerts can be via a mobile device such as a smartphone, or received via wireless signal or local Wi-Fi, from the Internet. The Internet need not necessarily be involved; the data could be communicated from a local server computer to the farmer's smartphone directly, via long-range Wi-Fi existing at the farm. However, a cloud-based server has several advantages and is preferred. Programming on the server can serve many farms, and is fairly sophisticated, with the ability to receive and manipulate many types of data and to present relevant status and maps as well as to retain historical data for the farmer, recallable when needed. Also, the cloud-based server enables the farmer to monitor conditions when away from the farm.

Figure 10:
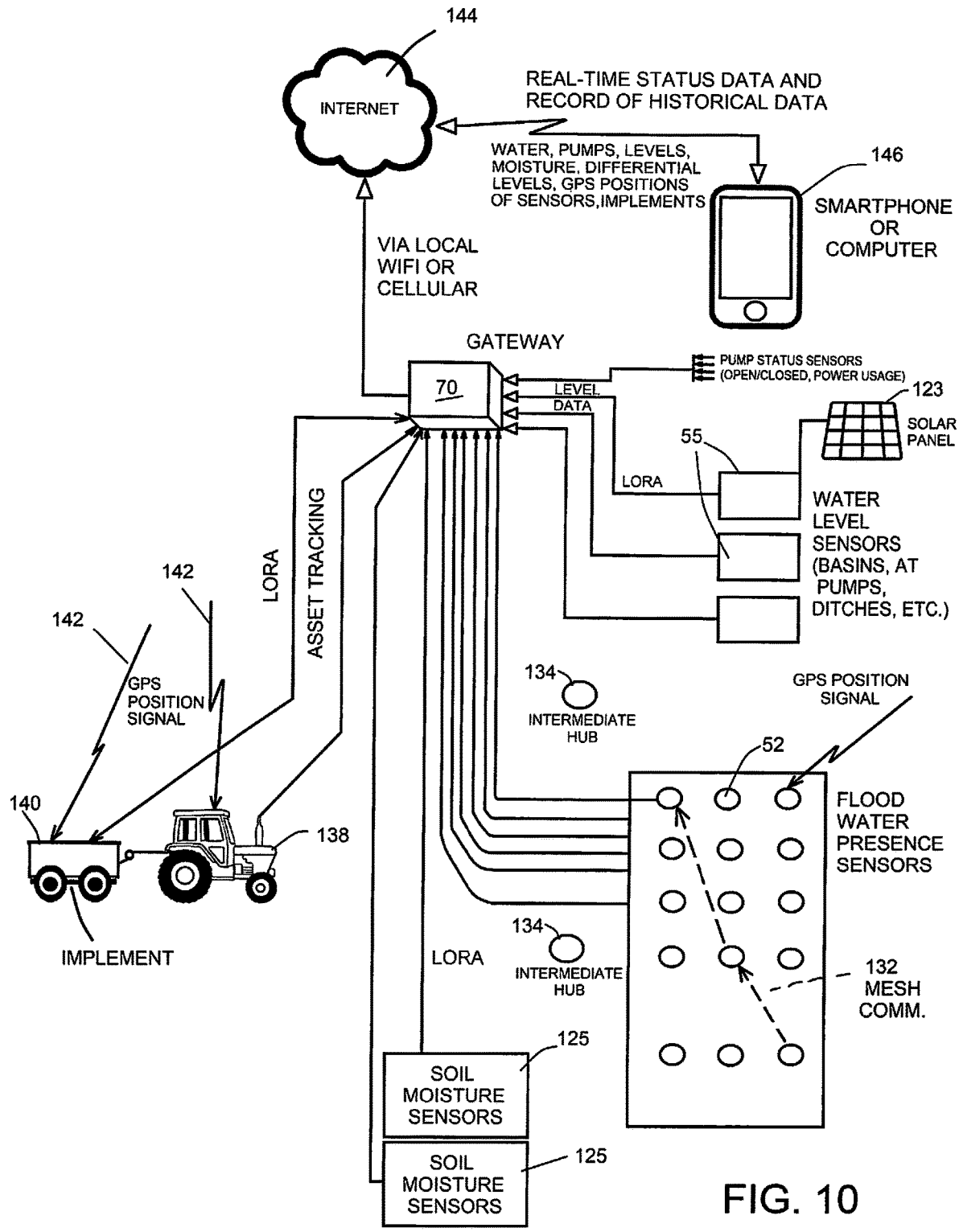
FIG. 10 is a block diagram showing inputs on a farm to a central hub or gateway and use of data from the inputs.

In the diagram of FIG. 10 the system of the invention is schematically illustrated. This diagram essentially expands on the simplified diagram of FIG. 4. The central hub or gateway is shown at 70, receiving data from a multitude of sources, all over local Wi-Fi, preferably long range Wi-Fi or LORA. Examples of data inputs are shown in the schematic. One (of several, or many) flood-irrigated field is shown at 30, with a series of the water presence sensors 52 positioned in the field. Wireless transmissions from these sensors to the gateway 70 are indicated. Optional "mesh" communication, from sensor 52 to sensor 52 and ultimately to the gateway, is indicated at 132. This has power drawbacks and more preferably intermediate hubs 134 can be positioned at strategic locations to carry the signals from the sensors 52 ultimately to the gateway 70, thus requiring lesser reach for the Wi-Fi communication. Each sensor 52 directly communicates to a hub 134, allowing the sensor 52 to power down, returning it to "sleep" mode and conserving battery. Hubs 134 will always be powered up, with batteries preferably charged by adjacent solar panels, so that battery usage at the hubs 134 is not an issue.

Water level sensors at indicated at 55 (with ultrasonic distance sensors 122), providing water level data for ditches, basins and boxes, and also differential levels where needed. As noted, solar panels 123 preferably are used to charge the batteries of the level sensors 55 so they can remain powered. This can also be the case with the soil moisture sensors 125. Pump status data is shown as sent to the gateway 70, as indicated at 136. Soil moisture sensors are indicated in the box 125, sending their signals when required to provide soil moisture content data. These sensors, shown in FIG. 9, can be similar to the soil presence sensors 52, with the same basic electronics by including the moisture sensing apparatus, such as illustrated in FIG. 9. Water level sensors and soil moisture sensors are best served by adjacent solar panels to recharge their batteries during the day. The box water level sensors preferably are always operational, not going into sleep mode. The same is preferably true of soil moisture sensors. In fact, these solar-recharged sensors can act as some or all of the intermediate hubs 134, if in strategic locations for the needed retransmissions.

Further, FIG. 10 shows a tractor 138, towing a farm implement 140, as an example of farm equipment that can be monitored as to position and use, each sending Wi-Fi signals (LORA) to the gateway 70 as requested. As discussed above, any number of farm implements and equipment can be monitored, each having GPS as noted at 142 in the drawing. The system can thereby provide data as to real-time position and movement of tractors and farm implements, and can maintain a historical database as to how much use each farm implement, particularly tractors, has had over a requested period of time, and what implements were towed by the tractor. With this information the farmer can appropriately rotate farm equipment to get maximum usage and life.

Also in the diagram of FIG. 10, the Internet with cloud server is denoted at 144; communication from and to the gateway 70 can be via local Wi-Fi or cellular communication. As illustrated, the server can provide information to the farmer via the smartphone 146 and/or via a portable or desktop computer of the farmer. As noted, these data can be real-time status data and/or historical data, regarding water presence, pumps, moisture, levels, differential water levels and GPS position of sensors and of farm implements, as discussed above.

Figure 11:
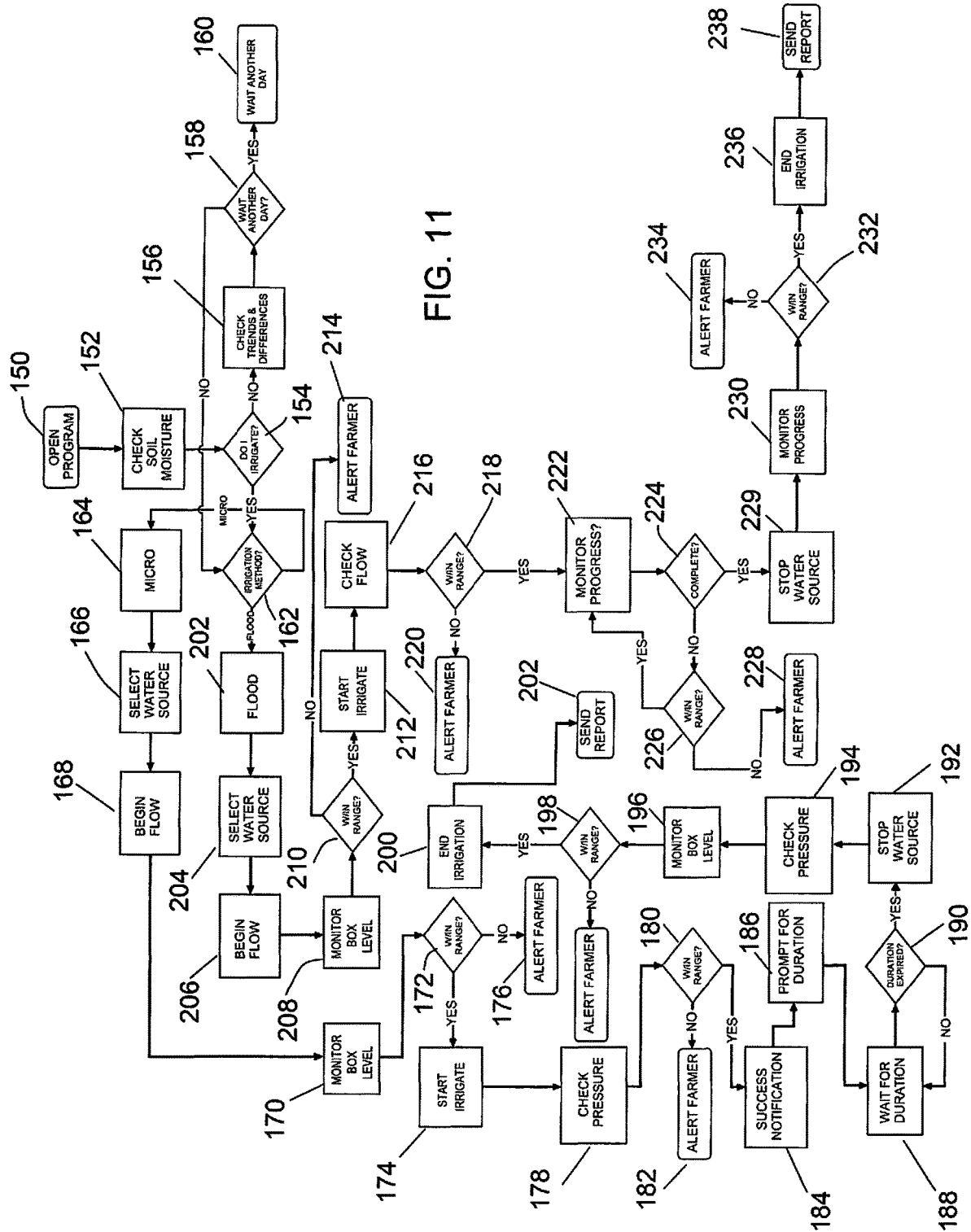
FIG. 11 is a flow chart outlining procedure on a farm for irrigating by flood and by micro irrigation.

The flow chart of FIG. 11 outlines the steps taken by a farmer in a typical crop watering scenario. The block 150 indicates opening the software of the system, which can be initiated by the farmer using a computer or a smartphone. This user interface connects to the database, preferably a cloud server. In this case the farmer checks soil moisture, indicated by the block 152, which can be by using electronic soil moisture monitors including the moisture probe features 130 as indicated in FIG. 9. The soil moisture is preferably reported at different depths, important for many crops depending on typical root penetration of the crop. For other fields without soil moisture probes, the farmer simply checks the fields by direct observation, and/or weather over the previous days or weeks and predicted weather, duration of time since the last watering, the nature of the soil in the field, recent temperatures and humidity, sun exposure and other relevant factors. The decision as to whether to irrigate is noted at 154. If the decision is negative, the farmer can examine historical data as to trends and differences in watering cycles, for help in making irrigation decisions going forward. This is noted at 156. The decision might be to wait one more day, as noted at 158 and 160, and if the decision is not to wait another day (based on the trends and differences observed), the flow goes to the decision block 162, where irrigation method is selected. For micro irrigation (block 164), as in spraying with sprinklers or drip irrigation, driven by a pump, the farmer selects the water source or sources to be used (166). In a system of irrigation pipes or ditches as the supply of water, the farmer may need to contact the irrigation district as to the availability of water, and request a desired flow rate or quantity of water. If sufficient water is not available, available well water can be used alone or in combination with district water.

The block 168, "begin flow", indicates the beginning of water delivery. In an irrigation district the source could be one or several miles away, upstream of the farm. A gate will be opened, typically by an irrigation district person. Depending on the distance of the gate from the farm, it might require several hours before the water arrives at the farm. Because the time of water arrival is not precisely known, the farmer monitors a box level, as noted in the block 170, to determine when the water is available at the farm. This can be done with an automatic alert to the farmer on a smartphone, from a signal sent by a device such as shown in FIG. 8, a distance sensor that will provide the farmer with water level in the box or in an irrigation canal or ditch. When the water rises in the box, and reaches the desired range as needed for the irrigation (decision block 172), the irrigation is started, as noted in the block 174. If the level of the water supply has not reached the desired range, the farmer can be alerted of this condition, as in the block 176, or he can simply be notified only when the water does reach the desired range.

Irrigation is commenced, and this is micro irrigation involving pumps, so the block 178 denotes that the farmer checks pressure in pipes. This can involve several check points and is provided so the farmer can assure that pressure is within the desired and safe range, as noted in the decision block 180. For example, if irrigation water is being pumped out at too great a flow rate, faster than the water is being delivered to the box, this will cause a problem and can be indicated by pressure or water level upstream of the pump. If pressures are too high in pipes downstream of the pump, this can indicate a blockage or partial blockage, at a filtration point or at some of the irrigating nozzles. Any blockages or high resistance downstream of the pump can present a danger of burst pipes and must be addressed by the farmer.

The block 182 notes that the farmer is alerted to any out-of-range pressures. If pressures are within range, this is indicated to the farmer (block 184), and at this point the farmer can be prompted to indicate a duration for this irrigation cycle, block 186.

Irrigation continues for the selected duration (block 188), and, when the duration has expired (block 190), the water flow is stopped at the source (192), i.e. the source of the pipe or ditch irrigation water which might be upstream several miles. Again, pressure and levels preferably are monitored, as noted in the blocks 194 and 196, to be sure the system shuts down properly. In the gravity system of delivering irrigation water to a number of farms, as is the case here, water coming down the ditch or pipe to the farm must be used, and thus irrigation continues until levels and pressures are safe and within ranges, as in the decision block 198. When this point is reached, irrigation is terminated (200), and a report (202) is sent to the farmer (received on a smartphone or computer), reporting the duration of the irrigation, approximate number of acre feet used, and how many flushes have occurred.

Backflushing is required for filters used to remove particulates from water to be used in irrigation. These includes sand filters and other types of filters, subject to clogging if not periodically backflushed. Different water sources have different filtration needs and are an important factor in determining how often the system will need to flush filters. Well water typically is cleaner than canal or ditch water. The system of the invention preferably operates backflushing not based on time intervals, which can waste a considerable amount of water by backflushing when not needed. The system described herein does not initiate flushing based on time, but rather on differential pressures and also based on the water source; well water will need very little filter flushing. By monitoring differential pressures upstream and downstream of the filter, the purer nature of well water is automatically accounted for.

Going back to the block 162, when the irrigation method is flood irrigation (block 202), again the water source to be used is selected, as noted at 204, and flow begins (206), which again may be from a source far upstream, requiring the opening of a gate. The farmer checks the box level (208), and steps 210, 212, 214 are similar to those described with respect to the blocks 172, 174 and 176. Here, flood irrigation is carried out by gravity flow, so the farmer checks the water flow, at block 216. The farmer needs verification that water level in the box, once present, is at a high enough level but not too high. Differential level sensors, as discussed above, can be used to provide more information, not only as to level but rate of flow, as by monitoring level both upstream and downstream of the farmer's gate, in a box.

If the flow is outside of an acceptable range (decision block 218), the farmer is alerted (220), as on a computer or a smartphone. Once the flow is within limits, the progress of the flood irrigation in one or more fields is monitored, see block 222. For this function the water presence sensors 52 described above can advantageously be used. If desired, the farmer can be presented, on a computer or smartphone, with a real-time map showing which sensors in a field are wet and which remain dry. As discussed earlier, there can be many sensors in a field, for higher resolution of data to the farmer.

At the decision block 224 the query is whether irrigation of the field is complete, but this is actually a projection as to whether it appears to be complete at this point. If not, and progress is not within range (decision block 226), the farmer is notified (228). If irrigation of a field is taking too long, the farmer will want to inspect to determine what has gone wrong. If the irrigation is within range (but not yet fully complete), again progress is monitored, and when the irrigation appears to be essentially complete the water is shut off at the source (unless another field is to be irrigated); see block 229. If the water source is distant as discussed above, water will continue to be delivered for a time. If the source is local, such as from ground water, then no projections need be made and the water source can simply be switched to another field or different portion of a field, for example.

The block 230 denotes that, in the case of a distant water source, the progress of the irrigation continues to be monitored, to be sure irrigation of the field is completed. If the irrigation data is not within range (232), again the farmer is alerted (234). If the irrigation is complete and within range, it is terminated, as at 236. Again, a report is sent to the farmer (238) providing all data on irrigation duration, the quantity of water used and any irregularites.

As noted above, the invention also encompasses monitoring water use beyond a single farm, including status of water in pipes, canals or ditches, volumetric flow rate of water through such water delivery conduits, and also monitoring indications of groundwater replenishment in a region where groundwater depletion is a concern. Some or all of the farms may employ surface water for flood irrigation and/or groundwater for micro irrigation. In addition, groundwater replenishment can be estimated via soil moisture content, especially where flood irrigation is used but also where micro irrigation is used. All monitoring can be via electronic devices on the farms and along water delivery canals, ditches or pipes, with wireless data transmission capability so as to enable monitoring at a central location.

Figure 12:
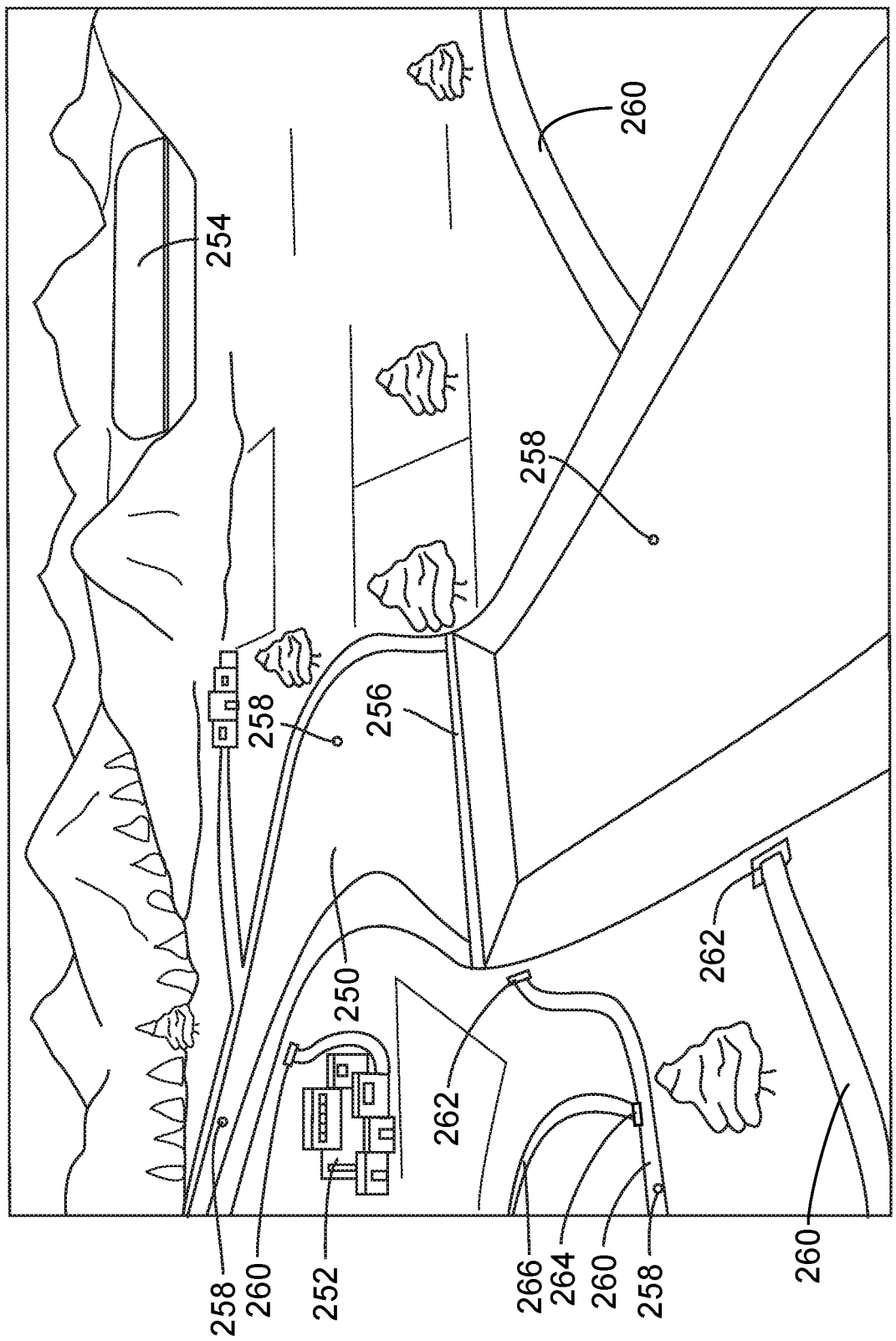
FIG. 12 is a pictorial view in perspective showing a surface water source such as an irrigation canal, with a series of lateral canals or ditches serving farms or groups of farms for irrigation.

FIG. 12 schematically illustrates, in a generalized pictorial view, a part of an irrigation system in which a river or canal or other surface water source 250 provides water to a plurality of water users located in the vicinity of the water source 250. This could be primarily irrigation water serving a number of farms, as indicated in the drawing, and it can also include industry, such as indicated at 252. The pictorial diagram indicates a reservoir at 254, which could be the source of the water in the canal 250.

The view of FIG. 12 indicates use of water level sensors, as well as weirs and gates that control flow of water, and flow measurement devices. All level and flow measurement devices are preferably wireless communication enabled, so that conditions can be monitored from a central location. The weir shown at 256 in the river or canal 250 is used to regulate downstream flow. Water surface level can be reported at several locations noted at 258 along the waterway 250, both above and below the weir. As discussed above, these water level detectors can comprise ultrasonic level sensors, each of which preferably being equipped with wireless data transmission capability.

Water is distributed via various canals, ditches or pipes, as shown at 260. For this purpose a lateral distribution gate 262 is positioned where water is released from the canal 250 to the lateral canal or ditch 260. Downstream gates are provided from the canal or ditch 260, such as at 264, for admitting water to individual farms or fields via a lateral ditch or pipe 266. If desired the position of the gates such as at 264 can be monitored via an electronic indicator at the gate, with wireless data transmission capability.

As water flows through the main river or canal 250, water level sensors 258 report to the central location surface levels at specific locations. Those locations can be given thresholds, and when water level is outside those thresholds alerts can be activated. This helps provide more accurate water distribution as well as advance warning of potential danger in the system, to prevent damage to the canals, ditches or pipes that deliver water as well as surrounding areas and facilities. At various locations, such as at the weir 256 and at gates 262 and 264, volumetric flow measuring devices can be installed to provide accurate data on flows of water in the system, for purposes of allocation, billing and also safety.

Figure 13:
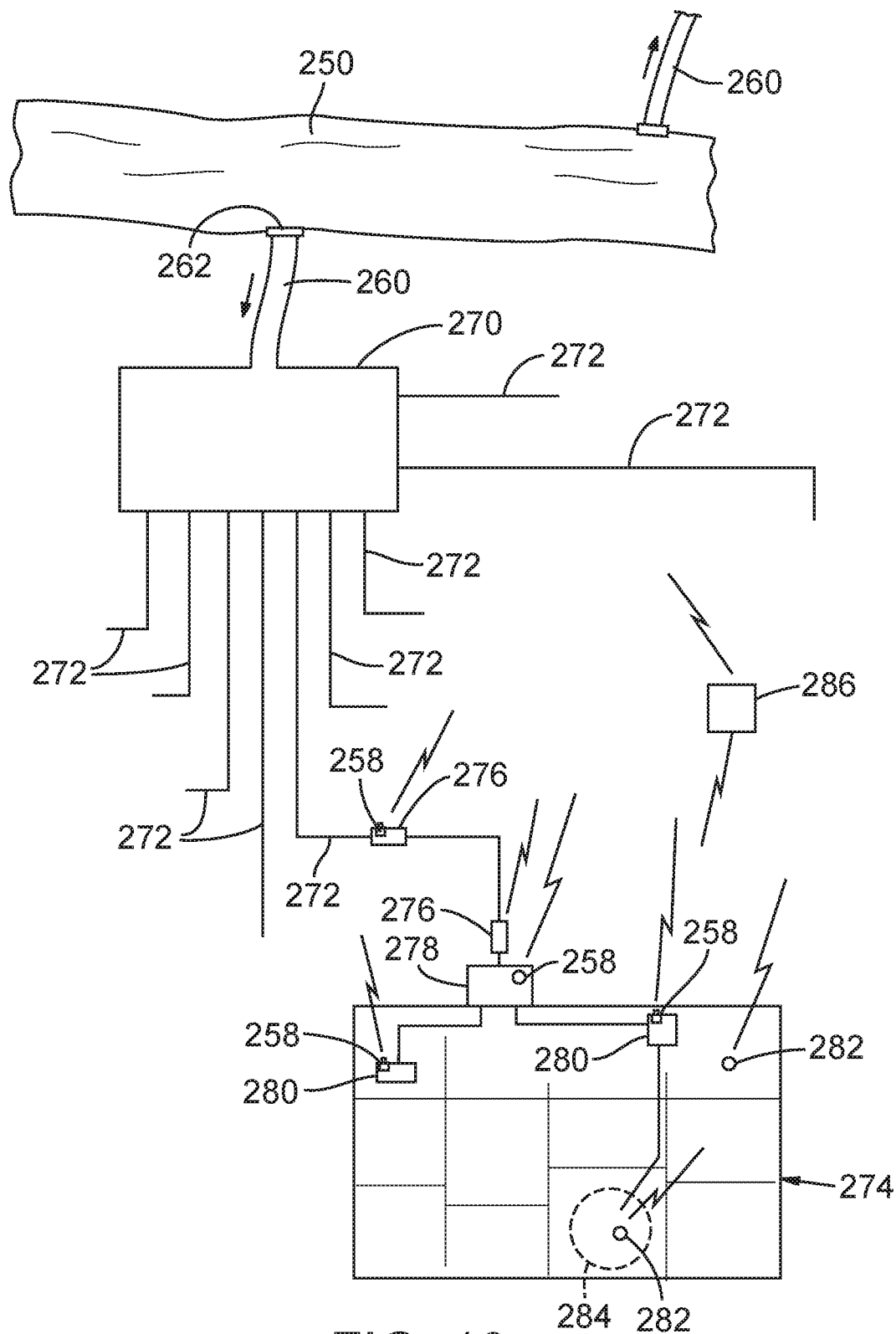
FIG. 13 is a schematic view indicating an example of an irrigation water district or system that delivers surface irrigation water to a plurality of distribution points, from which water is delivered to farms or groups of farms via canals, ditches or pipes, and indicating monitoring according to the invention.

FIG. 13 provides a schematic showing important aspects of the system of the invention. Again, a river or canal (or possibly a reservoir) is shown at 250. One primary lateral canal shown at 260 delivers water to a distribution location 270, which can be an irrigation district as noted in the drawing, which might serve thousands or tens of thousands of acres. For purposes of illustration this distribution site 270 can be considered a central location or headquarters that receives wireless data from a large number of sources indicating water status, water usage, gate or valve positions and in some cases, groundwater replenishment.

The drawing indicates a large number of irrigation water delivery laterals 272 which can be canals, ditches or pipes or combinations thereof, emanating from the distribution facility 270.

One farm in this acreage is indicated at 274, receiving water from a branch ditch, canal or pipe 272. Water level sensors 258 and/or volumetric flow measuring devices 276 can be located at desired positions along the ditch or pipe. Where the water reaches the farm an inflow box or basin 278 can be provided, preferably with a gate, and including an electronic water level monitor 258.

As noted, the farm 274 is an example of a farm that applies flood irrigation to at least some of the fields, received via the ditch or pipe 272, and also utilizes groundwater, which may be as a backup or a primary source of irrigation water, as in micro irrigation. The farm can be similar to the farm outlined in the embodiments described earlier. On the farm one or more boxes or basins 280 are downstream of the inlet basin 278, and each can be fitted with a water level sensor 258. As explained in the embodiments described above, these level sensors, each equipped with wireless data transmission electronics, enable efficient water management on the farm. The wireless transmission capability at the sensors is preferably at least one quarter mile.

Another feature of the invention, as noted above, is the monitoring of water seepage down through the soil, particularly on a farm such as at 274, as an indicator of replenishing groundwater supply. At strategic locations on the farm, subsurface moisture sensors, generally indicated at 282, are placed for this purpose. One of the subsurface moisture sensors is shown at a dedicated groundwater replenishment basin 284 that can be located on the farm. Such a replenishment basin 284, several or many of which can be located in the irrigation district, on farms or other locations, can receive not only rainwater but also deliberate flows of water from the distribution source 270 via the pipe or ditch 272, for recharge of groundwater in a season when water is relatively abundant, thus deliberately using this water to replenish groundwater rather than allowing the water to run off via surface drainage ultimately to streams or rivers. Groundwater is a critical issue in most irrigated parts of the U.S., and its use and replenishment are controlled by law in some jurisdictions. As described above, each of these monitoring devices 282, 258 and 276 can be provided with wireless electronic data transmission, to be received at a central location such as the facility 270, or any other monitoring station in the vicinity. Wireless transmission can be indirect, first received at one or a plurality of wireless data hubs 286 as shown in FIG. 13, with the data signals to be retransmitted from the wireless hub 286 to the central location, which can be the facility 270.

Figure 14:
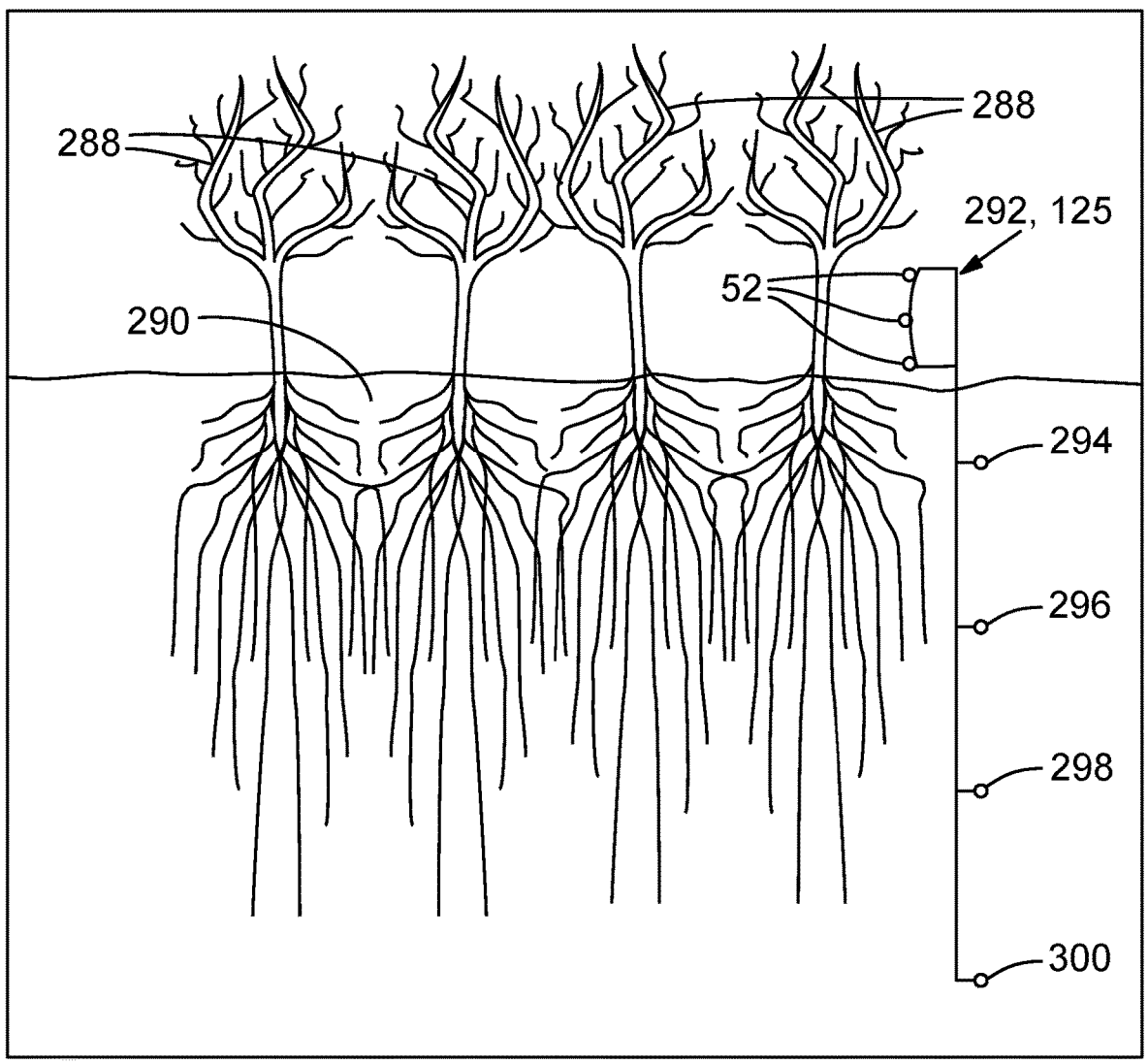
FIG. 14 is a schematic view in sectional elevation, illustrating equipment and a method for monitoring seepage of irrigation water downward through soil, below the level of plant roots, potentially replenishing groundwater, utilizing a series of moisture sensors at different levels.

FIG. 14 shows the soil moisture content monitoring, for the purpose of determining groundwater replenishment, in greater detail. In this schematic cross section view, plants, e.g. crops, are shown at 288, planted in the soil 290 of a field, e.g. a farm field. Above ground water detection is shown at 292, using one or more water presence detectors 52 described above, here shown sensing at three different levels above the surface of the field, so as to indicate depth. The three detection points can be in a single housing unit 125 such as shown in FIG. 9, with a series of water depth points. FIG. 14 also shows subsurface moisture detection at a series of different depth points 294, 296, 298 and 300. These also can be part of the same device 125 of FIG. 9, with electronics for both water presence/water depth detection and moisture detection at multiple levels, all such electronics being contained in the housing 125. In addition, the housing includes wireless transmission electronics, as explained above, for providing data signals to be transmitted over a long distance (with or without intermediate hubs for re-transmitting signals) to a central monitoring location. As an alternative, the moisture detectors could be any of several commercial and well known devices, such as Decagon EC-5 (Decagon Devices Corp., Pullman, Wash.) or Irrometer Watermark 200 SS (Irrometer Co., Riverside, Calif.).

In operation of the system, surface water is applied in abundance in flood irrigation, in amounts greater than what the existing vegetation can use. The water presence/depth measurement device 52 provides information on depth of water in the field, primarily for use of the farmer. Alternatively, water is applied by spraying, or micro irrigation. As water is absorbed down into the soil, it will pass through the root zones. The subsurface moisture sensors 294, 296 and 298 can be used to monitor takeup of water by the plants, providing feedback useful to the farmer in fine tuning amounts of water to be applied in different fields. These moisture sensors also indicate dryness of the soil between flood applications, and the need for watering.

Below the root zone of the plants, the sensor 300 detects excess water beyond that taken up by the plants, migrating down toward the water table. This indicates groundwater recharge. The amount of the recharge or replenishment taking place over time can be roughly calculated based on a number of factors, including the type of soil and the character of subsurface strata. As mentioned above, this same subsurface measurement method can be used at groundwater replenishment basins, on farms or elsewhere.

Estimated groundwater replenishment can be balanced against a farm's (or group of farms') water use, for credits against restrictions on use or other purposes.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A method for monitoring replenishment of groundwater on an irrigated farm or group of farms or another land area subject to groundwater depletion, comprising:
    installing moisture sensor devices below grade at a plurality of locations on a farm or group of farms, with sensor probes at a series of subsurface depths including below root levels of any vegetation,
    the moisture sensor devices having wireless data transmission capability for transmission of moisture content data signals over a distance, and
    at a monitoring location remote from the farm or land area, monitoring soil moisture content at a series of depths and at plural locations on the farm or farms or other land area using data as transmitted by the moisture sensor devices, so that replenishment of groundwater at the farm or farms can be determined by moistening of subsurface soils, including below roots, indicating migration of water down to a water table, thereby providing information useful in balancing water use, including groundwater use, against an estimated replenishment of groundwater by water seepage through subsurface soil down to the water table.

2. The method of claim 1, on a farm or farms which utilize surface irrigation water delivered in a pipe, ditch or canal, and wherein depth of water in the pipe, ditch or canal is monitored by wireless distance measuring devices positioned above a water surface in the pipe, ditch or canal, utilizing ultrasonic transmission or radar, each of the distance measuring devices having wireless data transmission capability for transmitting water level data over a distance such as to be received at the monitoring location, so that delivery of irrigation water on the farm or farms and status of water in the pipe, ditch or canal can be monitored, along with estimated groundwater replenishment at the farm or farms.

3. The method of claim 2, wherein volumetric flow of water through the pipe, ditch or canal is also monitored by flow measurement equipment having wireless data transmission capability over a distance such as to be received at the monitoring location, whereby irrigation water use at the farm or farms can be compared against said estimated replenishment of groundwater.

4. The method of claim 2, wherein the farm or farms include at least one groundwater replenishment basin, wherein a portion of the delivered irrigation water at the farm or farms can be diverted into the groundwater replenishment basin, at least one of said moisture sensor devices being positioned below ground at the groundwater replenishment basin.

5. The method of claim 1, wherein the farm or farms or other land area include at least one groundwater replenishment basin, wherein a portion of the delivered irrigation water at the farm or farms can be diverted into the groundwater replenishment basin, at least one of said moisture sensor devices being positioned below ground at the groundwater replenishment basin.

6. The method of claim 1, wherein transmissions of moisture content data to the monitoring location are indirect, first received at one or more wireless hubs, then relayed via a network to the monitoring location.

7. The method of claim 2, wherein the water level data are tied to geographic location of each distance measuring device.

* * * * *